United States Patent
Wang et al.

(10) Patent No.: US 12,258,703 B2
(45) Date of Patent: Mar. 25, 2025

(54) METHOD FOR PREPARATION OF PLASMA-TREATED NANOFIBER-BASED HYDROGEN GAS SENSING MATERIAL

(71) Applicant: CHONGQING UNIVERSITY, Chongqing (CN)

(72) Inventors: Feipeng Wang, Chongqing (CN); Kelin Hu, Chongqing (CN); Zijia Shen, Chongqing (CN); Hongcheng Liu, Chongqing (CN); Jianglin Xiong, Chongqing (CN); Jian Li, Chongqing (CN); Youyuan Wang, Chongqing (CN); Weigen Chen, Chongqing (CN); Lin Du, Chongqing (CN); Kaizheng Wang, Chongqing (CN); Qi Zhao, Chongqing (CN)

(73) Assignee: CHONGQING UNIVERSITY, Chongqing (CN)

( * ) Notice: Subject to any disclaimer, the term of this patent is extended or adjusted under 35 U.S.C. 154(b) by 318 days.

(21) Appl. No.: 17/906,072

(22) PCT Filed: Dec. 24, 2020

(86) PCT No.: PCT/CN2020/138764
§ 371 (c)(1),
(2) Date: Sep. 11, 2022

(87) PCT Pub. No.: WO2021/179735
PCT Pub. Date: Sep. 16, 2021

(65) Prior Publication Data
US 2023/0116126 A1    Apr. 13, 2023

(30) Foreign Application Priority Data

Mar. 12, 2020  (CN) .......................... 202010168936.0

(51) Int. Cl.
*D01D 1/02* (2006.01)
*D01D 5/00* (2006.01)
(Continued)

(52) U.S. Cl.
CPC ............ *D06M 10/025* (2013.01); *D01D 1/02* (2013.01); *D01D 5/003* (2013.01); *D01D 10/02* (2013.01);
(Continued)

(58) Field of Classification Search
CPC ....... D06M 10/025; D01D 1/02; D01D 5/003; D01D 10/02; D01F 6/26; D10B 2321/08
(Continued)

(56) References Cited

U.S. PATENT DOCUMENTS

| | | | |
|---|---|---|---|
| 2006/0293169 A1 | 12/2006 | Srinivasan et al. | |
| 2016/0240709 A1* | 8/2016 | Sung | H01L 31/0749 |
| 2019/0154645 A1 | 5/2019 | Kim et al. | |

FOREIGN PATENT DOCUMENTS

| | | |
|---|---|---|
| CN | 101786600 A | 7/2010 |
| CN | 102650083 A | 8/2012 |

(Continued)

OTHER PUBLICATIONS

International Search Report and Written Opinion mailed Mar. 22, 2021, in connection with International Patent Application No. PCT/CN2020/138764, filed Dec. 24, 2020, 12 pgs. (including translation).

*Primary Examiner* — Jeffrey M Wollschlager
*Assistant Examiner* — Xue H Liu
(74) *Attorney, Agent, or Firm* — Chiesa Shahinian & Giantomasi PC

(57) ABSTRACT

The present disclosure provides a preparation method of a plasma-treated nanofiber-based hydrogen gas sensing material, including the following steps: (1) stirring a mixed
(Continued)

solution of absolute ethanol, polyvinyl pyrrolidone (PVP), N,N-dimethylformamide, $SnCl_2 \cdot H_2O$, and $Zn(CH_3COO)_2 \cdot 2H_2O$ uniformly on a constant-temperature magnetic stirrer to obtain a spinning solution; (2) electrospinning the spinning solution and depositing on an aluminum foil to obtain a spinning fiber; (3) annealing the spinning fiber in a muffle furnace to obtain a hydrogen gas sensing material sample; and (4) subjecting the hydrogen gas sensing material sample to a vacuum argon plasma treatment with a Hall ion source to obtain the nanofiber-based hydrogen gas sensing material. In the method, nanofibers are prepared by electrospinning and subjected to the vacuum argon plasma treatment through the Hall ion source. The prepared sensing material has an extremely large specific surface area, and gas-sensing properties of rapid response and high sensitivity to hydrogen gas.

6 Claims, 2 Drawing Sheets

(51) Int. Cl.
*D01D 10/02* (2006.01)
*D01F 1/10* (2006.01)
*D01F 6/26* (2006.01)
*D06M 10/02* (2006.01)
*G01N 33/00* (2006.01)
*D06M 101/18* (2006.01)

(52) U.S. Cl.
CPC .................. *D01F 1/10* (2013.01); *D01F 6/26* (2013.01); *G01N 33/005* (2013.01); *D06M 2101/18* (2013.01); *D10B 2321/08* (2013.01); *D10B 2401/16* (2013.01); *D10B 2505/00* (2013.01)

(58) Field of Classification Search
USPC ....................................................... 264/483
See application file for complete search history.

(56) References Cited

FOREIGN PATENT DOCUMENTS

| | | | | |
|---|---|---|---|---|
| CN | 103553119 A | 2/2014 | | |
| CN | 105699440 A | 6/2016 | | |
| CN | 108774760 A | 11/2018 | | |
| CN | 109503879 A | * 3/2019 | ................ | C08J 7/06 |
| CN | 110346421 A | 10/2019 | | |
| CN | 110672672 A | 1/2020 | | |
| CN | 110702745 A | 1/2020 | | |
| CN | 111349974 A | 6/2020 | | |

* cited by examiner

METHOD FOR PREPARATION OF PLASMA-TREATED NANOFIBER-BASED HYDROGEN GAS SENSING MATERIAL

CROSS-REFERENCE TO RELATED APPLICATION

This application is a National Stage application under 35 U.S.C 371 of PCT/CN2020/138764, filed Dec. 24, 2020, which claims priority to Chinese Patent Application No. 202010168936.0, filed Mar. 12, 2020, the disclosures of all of which are incorporated herein by reference in their entirety.

TECHNICAL FIELD

The present disclosure relates to the technical field of gas sensors, and relates to a method for the preparation of a plasma-treated nanofiber-based hydrogen gas sensing material.

BACKGROUND

Hydrogen gas is known as the three major new energy sources together with solar energy and nuclear energy due to high combustion efficiency and non-polluting products. As a new energy, hydrogen gas is widely used in aerospace, power and other fields. However, hydrogen gas is prone to leakage during production, storage, transportation, and use due to an extremely small molecular structure. Moreover, hydrogen gas is colorless, odorless, hardly noticeable, and has a low ignition point and explosion limit, thus it can easily cause an explosion when encountering an open flame. Therefore, during use, hydrogen gas sensors are required to detect hydrogen gas content in the environment and monitor leakage of the hydrogen gas. Gas sensing materials is the key to the hydrogen gas sensors, and the response characteristics of the gas sensing materials to hydrogen gas directly effect the performance of the sensors. Therefore, there is a need in the art to improve the sensor performance by using a sensitive layer material with high-sensitivity hydrogen gas sensing properties.

At present, the preparation of hydrogen gas sensing materials with high sensitivity is a research hotspot. Nanostructures are prepared mainly by hydrothermal methods to increase a specific surface area of gas adsorption, while a gas-sensing selectivity is improved through noble metal doping by the hydrothermal methods. Chinese patent CN201310522532.7 disclosed a hydrothermal method for preparing a flower-shaped microsphere/nanorod gas-sensing material with aluminum-doped tin dioxide, including the following steps: (1) dissolving a certain proportion of tin tetrachloride pentahydrate and aluminum trichloride hexahydrate in absolute ethanol, and dissolving a certain amount of sodium hydroxide in deionized water; (2) mixing obtained solutions under the action of a magnetic stirrer, and stirring at a medium speed for 20 min to 30 min; (3) transferring a stirred solution into a reactor, conducting a reaction for a certain period of time at a set temperature, and naturally cooling to a room temperature; and (4) conducting centrifugal washing and drying to obtain a tin dioxide-doped powder. Chinese patent CN201610118627.6 discloses a preparation method of a tungsten oxide nanoflower-based hydrogen gas sensor, including the following steps: (1) growing tungsten oxide nanowires on a substrate, and attaching a tungsten powder to a surface of the substrate; (2) growing the tungsten powder on the substrate into a tungsten oxide nanoflower structure; (3) heating and annealing the substrate, doping a noble metal on the tungsten oxide nanoflower structure to obtain a hydrogen gas sensor sensing material; and (4) preparing an electrode at each end of the hydrogen gas sensor sensing material, and conducting lead package to obtain the tungsten oxide nanoflower-based hydrogen gas sensor. The tungsten oxide nanoflower is grown on the substrate by a hydrothermal method, and then doped; and the preparation of most hydrogen gas sensing materials involves complex reactions and manipulations. The art simply, efficient, and stable methods to in prepare hydrogen gas sensing materials.

Therefore, it is necessary to develop a preparation method for plasma-treated nanofiber-based hydrogen gas sensing material. The method should be easy to operate, simple, and result in a stable and high-efficient hydrogen gas sensing material.

SUMMARY

An objective of the present disclosure is to provide a method for the production of a plasma-treated nanofiber-based hydrogen gas sensing material. The method should be easy to operate and simple, and result in a stable and high-efficient hydrogen gas sensing material. The method should also effectively improve a gas sensing performance.

In order to solve the above technical problems, the present disclosure provides a method to prepare a plasma-treated nanofiber-based hydrogen gas sensing material, including the following steps:

(1) stirring a mixed solution of absolute ethanol, polyvinyl pyrrolidone (PVP), N,N-dimethylformamide (DMF), $SnCl_2 \cdot H_2O$, and $Zn(CH_3COO)_2 \cdot 2H_2O$ uniformly on a constant-temperature magnetic stirrer to obtain a spinning solution;

(2) electrospinning the spinning solution and depositing on an aluminum foil to obtain a spinning fiber;

(3) annealing the spinning fiber in a muffle furnace to obtain a hydrogen gas sensing material sample; and (4) subjecting the hydrogen gas sensing material sample to a vacuum argon plasma treatment with a Hall ion source to obtain the nanofiber-based hydrogen gas sensing material.

By adopting the method, nanofibers are prepared by electrospinning and subjected to the vacuum argon plasma treatment through the Hall ion source. The prepared sensing material has an extremely large specific surface area, and rapid responding gas-sensing properties with high sensitivity to hydrogen gas.

Preferably, in step (1), the $SnCl_2 \cdot H_2O$ and the $Zn(CH_3COO)_2 \cdot 2H_2O$ may have a mass ratio of (1-1.6):(1-1.6), and the absolute ethanol, the DMF, and the PVP may have a volume ratio of (1-1.5):(1-1.5):(1-1.5).

Preferably, step (1) may include the following steps: mixing 0.5 g to 0.8 g of the $SnCl_2 \cdot H_2O$, 0.5 g to 0.8 g of the $Zn(CH_3COO)_2 \cdot 2H_2O$, 5 mL to 7.5 mL of the absolute ethanol, and 5 mL to 7.5 mL of the DMF, and stirring on the constant-temperature magnetic stirrer at 50° C. and 300 r/min; after mixing uniformly by the stirring, adding 5 mL to 7.5 mL of the PVP to an obtained mixture, and continuing stirring at 50° C. and 300 r/min for 6 h to mix uniformly, to obtain the spinning solution.

Preferably, in step (2), a temperature may be controlled at 40° C. to 60° C. and a relative humidity may be controlled at 35% before electrospinning; and the electrospinning may be conducted by a flat plate winding method, with a needle as a positive electrode at a voltage range of 10 kV to 15 kV, and the aluminum foil as a negative electrode at a voltage range of 2 kV to 3 kV. In the flat plate winding method, the spinning solution forms Taylor cones under the action of a space electric field, and nanofibers are formed at a needle tip; the nanofibers are deposited on the aluminum foil by an electric field force to form a nanofiber film; when a white dense film is formed on the aluminum foil, the spinning is completed. An electrospinning device includes mainly a propelling pump, a syringe, a high-voltage power supply, and a receiving device; positive and negative electrodes of the high-voltage power supply are connected to a syringe needle and the receiving device, respectively, and the receiving device may be in various forms, such as a static plane, a high-speed rotating drum, or a disc; spinning parameter settings and environmental conditions are crucial to the spinning. There are many factors affecting the preparation of nanofibers by electrospinning, and these factors include solution properties, such as viscosity, elasticity, electrical conductivity, and surface tension; control variables, such as a static voltage in a capillary, a potential at a capillary orifice, and a distance between the capillary orifice and a collector; and environmental parameters, such as solution temperature, air humidity and temperature in a spinning environment, and air velocity.

Preferably, in step (3), the spinning fiber may be annealed in a muffle furnace by the following three stages:
a first stage of heating: heating the muffle furnace from a room temperature to 600° C. within 3 h;
a second stage of maintaining a constant-temperature: maintaining the muffle furnace at 600° C. for 2 h; and
a third stage of cooling: reducing a power of the muffle furnace to 0, and naturally cooling to the room temperature.

Preferably, in step (4), the vacuum argon plasma treatment may include the following steps: placing the hydrogen gas sensing material sample into a vacuum chamber; conducting vacuumization with an air pump and a molecular pump to a vacuum degree of $5 \times 10^{-3}$ Pa, and introducing 3 sccm to 5 sccm of argon gas into the vacuum chamber to keep the vacuum degree at $1 \times 10^{-2}$ Pa to $5 \times 10^{-2}$ Pa; turning on the Hall ion source, adjusting an anode voltage and an anode current, starting timing, and recording a cathode voltage and a cathode current; when the treatment is completed, turning off the Hall ion source, introducing nitrogen gas, opening the vacuum chamber, and removing the sample to complete the vacuum argon plasma treatment; the vacuum argon plasma treatment may be conducted at a cathode voltage of 10 V to 15 V, a cathode current of 8.0 A to 10.0 A, an anode voltage of 120 V to 150 V, and an anode current of 1.0 A to 1.9 A for 5 min to 20 min.

Compared with the prior art, the present disclosure has the following beneficial effects: ZnO/SnO$_2$ nanofibers are prepared by electrospinning, and the vacuum argon plasma treatment is conducted by the Hall ion source to increase the specific surface area of the sensing material; the sensing material has an extremely large specific surface area, and has gas-sensing properties of rapid response and high sensitivity to the hydrogen gas. The plasma treatment can effectively reduce a hydrogen response temperature and improve a response sensitivity. The high-sensitivity hydrogen gas sensing material has a wide range of use, and can be used as a sensing material for various hydrogen gas sensors. The preparation method has desirable practicability, controllable procedures, simple steps, and strong repeatability.

DETAILED DESCRIPTION

Figure 1:
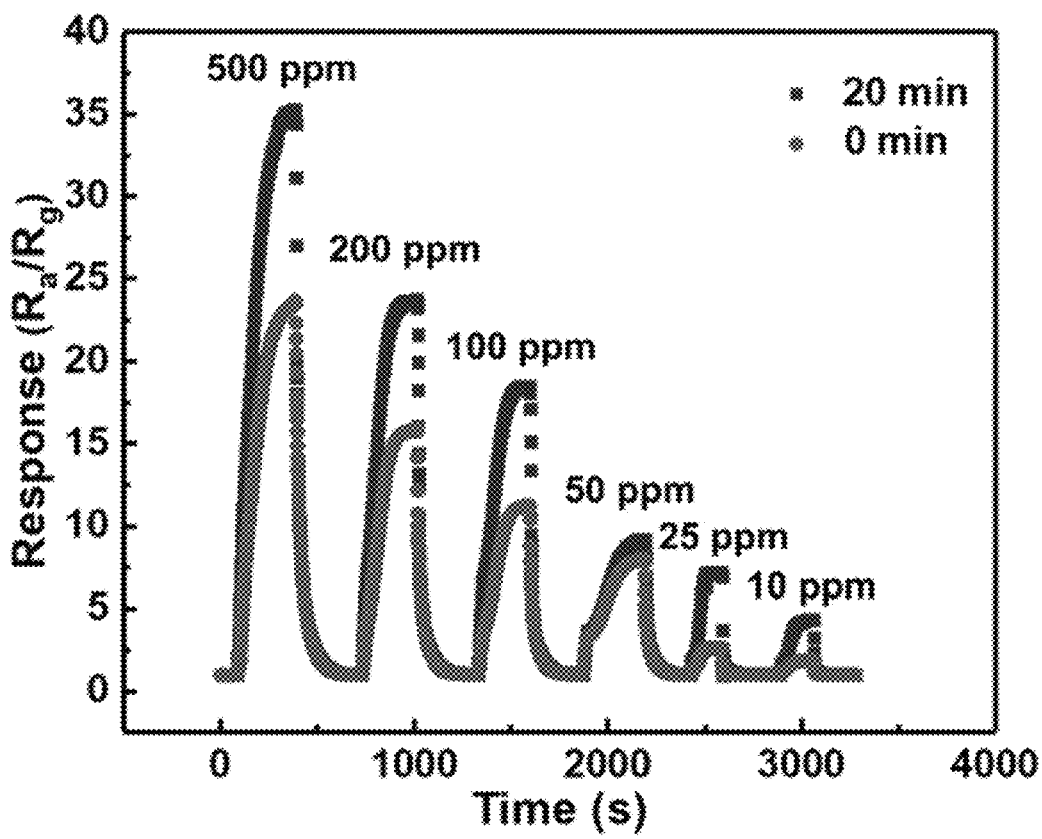
FIG. 1 shows a gas-sensing response characteristic comparison of a ZnO/SnO$_2$ nanofiber-based sensing material prepared by a preparation method for plasma-treated nanofiber-based hydrogen gas sensing material (Example 1) and a ZnO/SnO$_2$ nanofiber-based sensing material without plasma treatment (blank example)

Blank Example: a method of preparing a plasma-treated nanofiber-based hydrogen gas sensing material included the following steps:
(1) a mixed solution of absolute ethanol, PVP, DMF, SnCl$_2$·H$_2$O, and Zn(CH$_3$COO)$_2$·2H$_2$O were stirred uniformly on a constant-temperature magnetic stirrer to obtain a spinning solution;
in step (1), the SnCl$_2$·H$_2$O and the Zn(CH$_3$COO)$_2$·2H$_2$O had a mass ratio of 1:1, and the absolute ethanol, the DMF, and the PVP had a volume ratio of 1:1:1;
specifically, step (1) included the following steps: 0.5 g of the SnCl$_2$·H$_2$O, 0.5 g of the Zn(CH$_3$COO)$_2$·2H$_2$O, 5 mL of the absolute ethanol, and 5 mL of the DMF were mixed, and stirred on the constant-temperature magnetic stirrer at 50° C. and 300 r/min; after mixing uniformly by the stirring, 5 mL of the PVP was added to an obtained mixture, and continued stirring at 50° C. and 300 r/min for 6 h to mix uniformly, to obtain the spinning solution;
(2) the spinning solution was subjected to electrospinning and deposited on an aluminum foil to obtain a spinning fiber;
in step (2), a temperature was controlled at 50° C. and a relative humidity was controlled at 35% before electrospinning; and the electrospinning was conducted by a flat plate winding method, with a needle as a positive electrode at a voltage range of 15 kV, and the aluminum foil as a negative electrode at a voltage range of 3 kV;
(3) the spinning fiber was annealed in a muffle furnace to obtain a hydrogen gas sensing material sample; and
in step (3), the spinning fiber was annealed in a muffle furnace by the following three stages:
a first stage of heating: the muffle furnace was heated from a room temperature to 600° C. within 3 h;
a second stage of maintaining a constant-temperature: the muffle furnace was maintained at 600° C. for 2 h; and
a third stage of cooling: a power of the muffle furnace was reduced to 0, and naturally cooled to the room temperature; such that the nanofiber-based hydrogen gas sensing material was obtained.

Example 1: a preparation method of a plasma-treated nanofiber-based hydrogen gas sensing material included the following steps:
(1) a mixed solution of absolute ethanol, PVP, DMF, SnCl$_2$·H$_2$O, and Zn(CH$_3$COO)$_2$·2H$_2$O were stirred uniformly on a constant-temperature magnetic stirrer to obtain a spinning solution;
in step (1), the SnCl$_2$·H$_2$O and the Zn(CH$_3$COO)$_2$·2H$_2$O had a mass ratio of 1:1, and the absolute ethanol, the DMF, and the PVP had a volume ratio of 1:1:1;

specifically, step (1) included the following steps: 0.5 g of the $SnCl_2 \cdot H_2O$, 0.5 g of the $Zn(CH_3COO)_2 \cdot 2H_2O$, 5 mL of the absolute ethanol, and 5 mL of the DMF were mixed, and stirred on the constant-temperature magnetic stirrer at 50° C. and 300 r/min; after mixing uniformly by the stirring, 5 mL of the PVP was added to an obtained mixture, and continued stirring at 50° C. and 300 r/min for 6 h to mix uniformly, to obtain the spinning solution;

(2) the spinning solution was subjected to electrospinning and deposited on an aluminum foil to obtain a spinning fiber;

in step (2), a temperature was controlled at 50° C. and a relative humidity was controlled at 35% before the electrospinning; and the electrospinning was conducted by a flat plate winding method, with a needle as a positive electrode at a voltage range of 15 kV, and the aluminum foil as a negative electrode at a voltage range of 3 kV;

(3) the spinning fiber was annealed in a muffle furnace to obtain a hydrogen gas sensing material sample; and in step (3), the spinning fiber was annealed in a muffle furnace by the following three stages:

a first stage of heating: the muffle furnace was heated from a room temperature to 600° C. within 3 h;

a second stage of maintaining a constant-temperature: the muffle furnace was maintained at 600° C. for 2 h; and a third stage of cooling: a power of the muffle furnace was reduced to 0, and naturally cooled to the room temperature;

(4) an annealed hydrogen gas sensing material sample was subjected to a vacuum argon plasma treatment with a Hall ion source to obtain the nanofiber-based hydrogen gas sensing material. The nanofibers were prepared by electrospinning and subjected to the vacuum argon plasma treatment through the Hall ion source. The prepared sensing material had an extremely large specific surface area, and gas-sensing properties of rapid response and high sensitivity to hydrogen gas.

In step (4), the vacuum argon plasma treatment included the following steps: the hydrogen gas sensing material sample was placed into a vacuum chamber; vacuumization was conducted with an air pump and a molecular pump to a vacuum degree of $5\times10^{-3}$ Pa, and 4 sccm of argon gas was introduced into the vacuum chamber to keep the vacuum degree at $1\times10^{-2}$ Pa; the Hall ion source was turned on, an anode voltage and an anode current were adjusted, timing was started, and a cathode voltage and a cathode current were recorded; when the treatment was completed, the Hall ion source was turned off, nitrogen gas was introduced, the vacuum chamber was opened, and the sample was removed to complete the vacuum argon plasma treatment; the vacuum argon plasma treatment was conducted at a cathode voltage of 15 V, a cathode current of 8 A, an anode voltage of 145 V, and an anode current of 1.2 A for 20 min.

As shown in FIG. 1, FIG. 1 showed a gas-sensing response characteristic comparison of a $ZnO/SnO_2$ nanofiber-based sensing material prepared by a preparation method of a plasma-treated nanofiber-based hydrogen gas sensing material (Example 1) and a $ZnO/SnO_2$ nanofiber-based sensing material without plasma treatment (blank example); the square and circle points in FIG. 1 described the gas-sensing responses of the plasma-treated and untreated materials, respectively. It was seen that when a hydrogen concentration was 10 ppm to 500 ppm, a gas-sensing performance of the plasma-treated material was significantly better than that of the untreated material.

Figure 2:
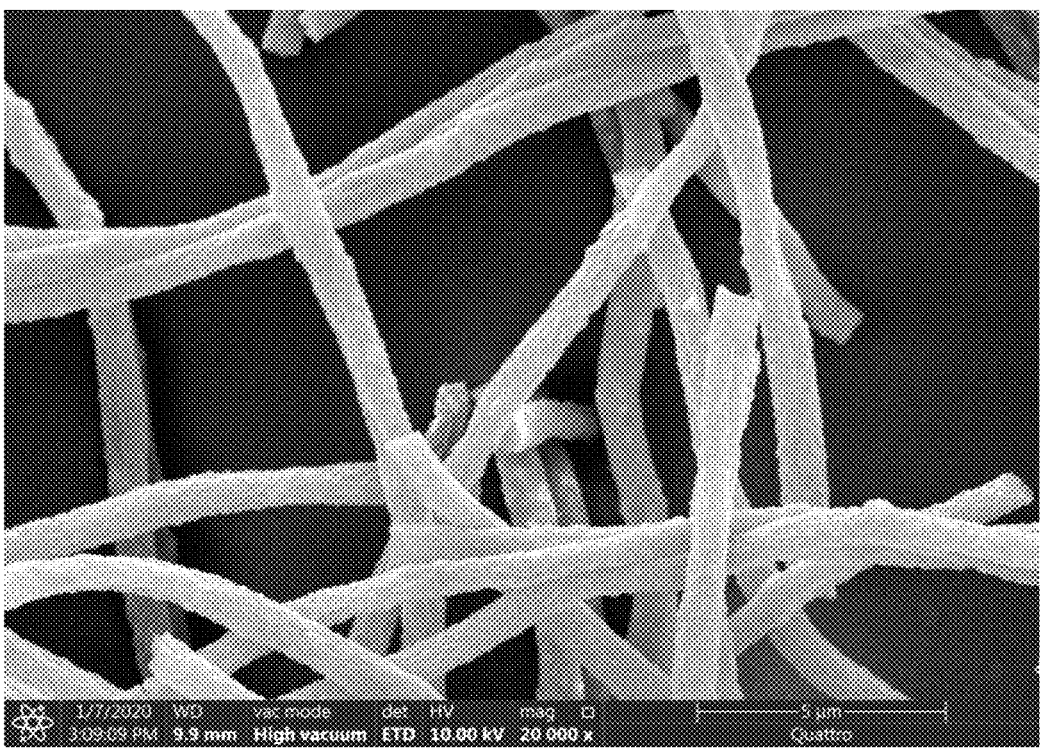
FIG. 2 shows a surface topography of the ZnO/SnO$_2$ nanofiber-based sensing material prepared by a preparation method of a plasma-treated nanofiber-based hydrogen gas sensing material (Example 1) under a field emission scanning electron microscope.

FIG. 2 shows a surface topography of the $ZnO/SnO_2$ nanofiber-based sensing material prepared by a preparation method of a plasma-treated nanofiber-based hydrogen gas sensing material (Example 1) under a field emission scanning electron microscope; it was seen from the figure that the plasma-treated $ZnO/SnO_2$ nanofiber-based sensing material has a continuous nanofiber shape, with a diameter of about 500 nm.

Figure 3:
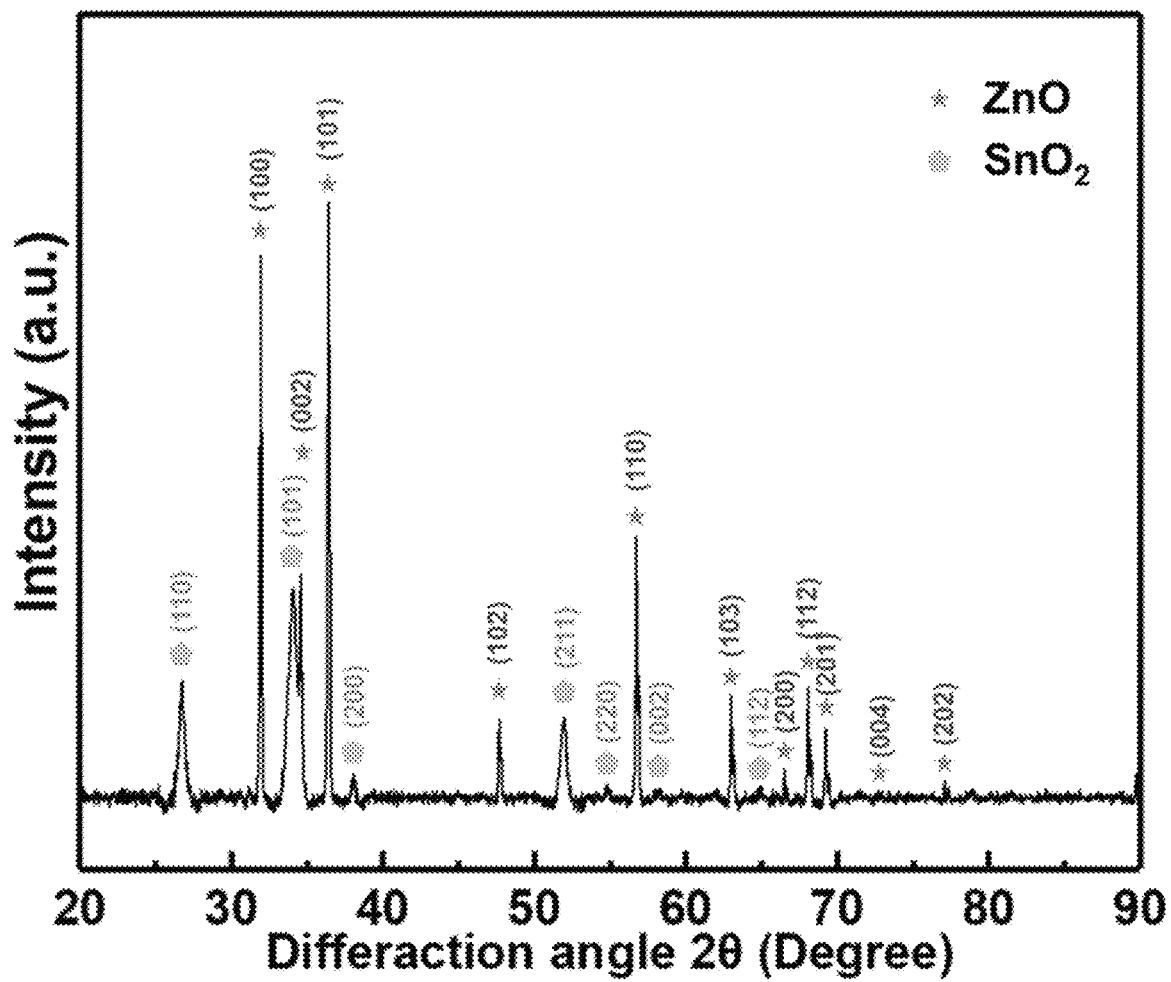
FIG. 3 shows an X-ray diffraction (XRD) pattern of the ZnO/SnO$_2$ nanofiber-based sensing material prepared by a preparation method of a plasma-treated nanofiber-based hydrogen gas sensing material (Example 1).

FIG. 3 showed an X-ray diffraction (XRD) pattern of the $ZnO/SnO_2$ nanofiber-based sensing material prepared by a preparation method of a plasma-treated nanofiber-based hydrogen gas sensing material (Example 1); the five-pointed star and pentagon in the figure represented each diffraction peak of $ZnO/SnO_2$, and from XRD characterization results, it was proved that the gas sensing material included $ZnO/SnO_2$.

The objectives, technical solutions, and beneficial effects of the present disclosure are further described in detail in the above specific examples. It should be understood that the above are merely specific examples of the present invention, but are not intended to limit the invention. Any modification, equivalent replacement, or improvement made within the spirit and principle of the present disclosure shall fall within the protection scope of the present disclosure.

What is claimed is:

1. A method for preparation of a plasma-treated nanofiber-based hydrogen gas sensing material, comprising the following steps:

(1) stirring a mixed solution of absolute ethanol, polyvinyl pyrrolidone (PVP), N,N-dimethylformamide (DMF), $SnCl_2 \cdot H_2O$, and $Zn(CH_3COO)_2 \cdot 2H_2O$ uniformly on a constant-temperature magnetic stirrer to obtain a spinning solution;

(2) electrospinning the spinning solution and depositing on an aluminum foil to obtain a spinning fiber;

(3) annealing the spinning fiber in a muffle furnace to obtain a hydrogen gas sensing material sample; and (4) subjecting the hydrogen gas sensing material sample to a vacuum argon plasma treatment with a Hall ion source to obtain the nanofiber-based hydrogen gas sensing material, wherein in step (1), the $SnCl_2 \cdot H_2O$ and the $Zn(CH_3COO)_2 \cdot 2H_2O$ have a mass ratio of (1-1.6):(1-1.6), and the absolute ethanol, the DMF, and the PVP have a volume ratio of (1-1.5):(1-1.5):(1-1.5), and wherein in step (4), the vacuum argon plasma treatment comprises the following steps: placing the hydrogen gas sensing material sample into a vacuum chamber; conducting vacuumization with an air pump and a molecular pump to a vacuum degree of $5\times10^{-3}$ Pa, and introducing 3 sccm to 5 sccm of argon gas into the vacuum chamber to keep the vacuum degree at $1\times10^{-2}$ Pa to $5\times10^{-2}$ Pa; turning on the Hall ion source, adjusting an anode voltage and an anode current, starting timing, and recording a cathode voltage and a cathode current; and when the treatment is completed, turning off the Hall ion source, introducing nitrogen gas, opening the vacuum chamber, and removing the sample to complete the vacuum argon plasma treatment; wherein the vacuum argon plasma treatment is conducted at a cathode voltage of 10 V to 15 V, a cathode current of 8.0 A to 10.0 A, an anode voltage of 120 V to 150 V, and an anode current of 1.0 A to 1.9 A for 5 min to 20 min.

2. The method for preparation of a plasma-treated nanofiber-based hydrogen gas sensing material according to claim 1, wherein step (1) specifically comprises the following steps: mixing 0.5 g to 0.8 g of the $SnCl_2 \cdot H_2O$, 0.5 g to 0.8 g of the $Zn(CH_3COO)_2 \cdot 2H_2O$, 5 mL to 7.5 mL of the absolute ethanol, and 5 mL to 7.5 mL of the DMF, and stirring the mixed solution on the constant-temperature magnetic stirrer at 50° C. and 300 r/min; after mixing uniformly by the stirring, adding 5 mL to 7.5 mL of the PVP to an obtained mixture, and continuing stirring at 50° C. and 300 r/min for 6 h to mix uniformly, to obtain the spinning solution.

3. The method for preparation of a plasma-treated nano-fiber-based hydrogen gas sensing material according to claim 1, wherein in step (2), a temperature is controlled at 40° C. to 60° C. and a relative humidity is controlled at 35% before the electrospinning; and the electrospinning is conducted by a flat plate winding method, with a needle as a positive electrode at a voltage range of 10 kV to 15 kV, and the aluminum foil as a negative electrode at a voltage range of 2 kV to 3 kV.

4. The method for preparation of a plasma-treated nano-fiber-based hydrogen gas sensing material according to claim 1, wherein in step (3), the spinning fiber is annealed in a muffle furnace by the following three stages:

a first stage of heating: heating the muffle furnace from a room temperature to 600° C. within 3 h;

a second stage of maintaining a constant-temperature: maintaining the muffle furnace at 600° C. for 2 h; and a third stage of cooling: reducing a power of the muffle furnace to 0, and naturally cooling to the room temperature.

5. The method for preparation of a plasma-treated nano-fiber-based hydrogen gas sensing material according to claim 1, wherein the vacuum argon plasma treatment is conducted at the cathode voltage of 14.2 V, the cathode current of 10.0 A, the anode voltage of 150 V, and the anode current of 1.9 A.

6. The method for preparation of a plasma-treated nano-fiber-based hydrogen gas sensing material according to claim 1, wherein the vacuum argon plasma treatment is conducted at the cathode voltage of 15 V, the cathode current of 8 A, the anode voltage of 145 V, and the anode current of 1.2 A for 20 min.

* * * * *